(12) United States Patent
Kroll et al.

(10) Patent No.: US 7,590,445 B1
(45) Date of Patent: Sep. 15, 2009

(54) INDIRECT MECHANICAL MEDICAL THERAPY SYSTEM

(75) Inventors: Mark W. Kroll, Simi Valley, CA (US); Russell Klehn, Valencia, CA (US); Brett Schleicher, Bend, OR (US); Reuben Westmoreland, Colfax, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 243 days.

(21) Appl. No.: 11/049,781

(22) Filed: Feb. 1, 2005

(51) Int. Cl.
*A61N 1/00* (2006.01)
(52) U.S. Cl. ......................................................... 607/4
(58) Field of Classification Search ................. 607/3–6, 607/116, 45; 600/16, 17; 623/3.12; 601/2
See application file for complete search history.

(56) References Cited

U.S. PATENT DOCUMENTS

| | | | | |
|---|---|---|---|---|
| 3,911,898 | A | * | 10/1975 | Leachman, Jr. .............. 600/17 |
| 4,651,716 | A | * | 3/1987 | Forester et al. .................. 601/2 |
| 5,222,980 | A | * | 6/1993 | Gealow ...................... 623/3.12 |
| 5,383,840 | A | * | 1/1995 | Heilman et al. ............... 600/17 |
| 5,935,158 | A | * | 8/1999 | Holmstrom et al. ......... 607/116 |
| 6,263,241 | B1 | * | 7/2001 | Rosborough et al. ........... 607/6 |
| 6,292,694 | B1 | | 9/2001 | Schloss et al. |
| 6,298,267 | B1 | * | 10/2001 | Rosborough et al. ........... 607/6 |
| 6,408,205 | B1 | * | 6/2002 | Renirie et al. .................. 607/5 |
| 6,510,342 | B1 | | 1/2003 | Park et al. |
| 6,519,493 | B1 | | 2/2003 | Florio et al. |
| 6,606,517 | B1 | | 8/2003 | Park et al. |
| 6,671,556 | B2 | * | 12/2003 | Osorio et al. ................. 607/45 |
| 6,694,188 | B1 | | 2/2004 | Kroll |
| 6,695,761 | B2 | | 2/2004 | Oschman et al. |
| 6,766,194 | B1 | | 7/2004 | Kroll |
| 6,775,571 | B1 | | 8/2004 | Kroll |
| 6,804,556 | B1 | | 10/2004 | Florio et al. |
| 7,050,849 | B2 | * | 5/2006 | Echt et al. ...................... 607/3 |
| 2003/0144572 | A1 | | 7/2003 | Oschman et al. |
| 2004/0260214 | A1 | | 12/2004 | Echt et al. |
| 2005/0119706 | A1 | * | 6/2005 | Ideker et al. ................... 607/5 |
| 2005/0131468 | A1 | | 6/2005 | Echt et al. ...................... 607/9 |

FOREIGN PATENT DOCUMENTS

| | | |
|---|---|---|
| EP | 1078649 A1 | 2/2001 |
| WO | WO 0113990 A1 | 3/2001 |
| WO | WO 2004112885 A2 | 12/2004 |
| WO | WO 2004112885 A3 | 12/2004 |
| WO | WO 2004112886 A2 | 12/2004 |
| WO | WO 2004113886 A3 | 12/2004 |

\* cited by examiner

*Primary Examiner*—George Manuel

(57) ABSTRACT

A device and methods for automatically evaluating one or more patient physiological parameters and, upon determination that certain therapies are indicated, delivering therapeutic mechanical stimulations to tissue of the patient. The mechanical stimulations generally include vibrations delivered at frequencies somewhat higher or lower than an intrinsic frequency and the therapeutic vibrations are delivered to drive the intrinsic frequency towards a desired value. The device and methods more closely emulate natural physiologic feedback mechanisms and can reduce undesired side effects of other known therapies. The device can include a small and efficient electrical motor which is interconnected with a crank and link mechanism to generate oscillatory motion which is conducted to a flexible wall of a bio-compatible housing of the device.

9 Claims, 11 Drawing Sheets

INDIRECT MECHANICAL MEDICAL THERAPY SYSTEM

FIELD OF THE INVENTION

The invention relates to the field of medical therapy devices and more particularly to devices and algorithms for automatically evaluating and providing indirect mechanical therapeutic stimulation to treat hypertension conditions and/or cardiac arrhythmias.

BACKGROUND OF THE INVENTION

A large number of people suffer from health conditions which are either directly or indirectly related to their cardiac function. For example, hypertension refers to a chronic disease in which the patient's systemic blood pressure is elevated above that which is considered a healthy level. As a chronic condition, hypertension can contribute to a wide variety of well known health ailments. Accordingly, therapy for a known hypertension condition is typically prescribed to ameliorate the hypertension condition and related effects. Depending on the severity of the hypertension as well as the patient's individual condition, typical therapies can include diet modification, an exercise regimen, and/or a medication regimen.

Another category of cardiac related health ailments include cardiac arrhythmias. A number of medications are known which can help restore, at least partially, more normal sinus rhythm for certain patients. Another known category of therapy for cardiac arrhythmias includes implantable cardiac stimulation devices, such as pacemakers and/or implantable cardioverter-defibrillators (ICDs). Implantable cardiac stimulation devices automatically monitor the ongoing cardiac activity of the patient and selectively provide direct electrical stimulation to the cardiac tissue when indicated in an attempt to restore the patient's intrinsic rhythm to a sinus rhythm or alternatively to substitute for the patient's intrinsic rhythm and assume control of the heart's activity for at least some period of time, such as in pacing. While implantable cardiac stimulation devices can be quite effective in treating cardiac arrhythmias, they are not generally considered appropriate therapy for patients with hypertension but without a history of cardiac arrhythmias.

A drawback to the use of implantable cardiac stimulation devices, such as pacemakers, as therapeutic interventions for cardiac related health ailments, such as cardiac arrhythmias, is that they are relatively crude in nature as compared to natural cardiac pacing in that they directly provide electrical stimulation to one or more chambers of the heart (atria/ventricles). This direct electrical stimulation acts as a surrogate for the native electro-chemically based natural pacing functions of the heart, however, this artificial electrical stimulation does not fully replicate the natural intrinsic stimuli which induce activity in the cardiac tissue.

The use of implantable cardiac stimulation devices for some patients can lead to a wide variety of symptoms known generally as "pacemaker syndrome." Pacemaker syndrome refers broadly to adverse hemodynamic and/or electro physiologic consequences associated with the presence of the artificial direct electrical stimulation in place of the natural intrinsic pacing of the patient. Pacemaker syndrome may be found on an intermittent or a persistent basis, and the severity of the symptoms can range from relatively minor to more severe, and can also be considered to include limitations on the patient's ability to achieve an otherwise optimal status. Pacemaker syndrome is frequently associated with a loss of appropriate atrial-ventricular (AV) synchrony, however, can also occur due to an inappropriate AV interval. Pacemaker syndrome can also arise from inappropriate rate modulation which refers to the modulation of the cardiac output, including heart rate, based on the patient's varying metabolic need.

Implantable cardiac stimulation devices provide therapy by detecting and discriminating relatively low amplitude complex time varying electrical signals from one or more heart chambers, evaluating these signals as well as other indications of the patient's physiological status, and delivering appropriate therapy to one or more chambers of the heart. Accordingly, implantable cardiac stimulation devices are relatively complex and expensive to design and produce. Their implantation also requires the expertise of highly trained and skilled clinicians as well as for periodic follow-ups to monitor the therapy and the patient's response for "fine-tuning" the device settings. Thus, implantable cardiac stimulation devices are a relatively costly therapy to provide and maintain both in terms of the devices themselves and the services of trained clinicians.

One possible approach to provide therapy while avoiding the physiologic and cost drawbacks of direct electrical stimulation of the cardiac tissue would be to provide some manner of indirect therapy or stimulation, such as provided by the body's natural feedback mechanisms. For example, providing stimulation to the vagus and/or sympathetic nerves has been considered as a possible avenue for therapy delivery. However, it has as yet proven impractical to access these nerves and to realize effective placement of leads on them to provide stimulation on a long term basis.

Thus, it will be understood that there is an ongoing need for providing interventional therapy for patient conditions, such as cardiac arrhythmia and/or hypertension, in a manner which reduces the negative consequences or side effects of known therapies. There is a desire for a therapy option which avoids the negative consequences of direct electrical stimulation of the cardiac tissue, such as the aforementioned pacemaker syndrome, as well as undesirable side effects attendant pharmacological therapies, such as adrenergic and/or anti-hypertensive drugs. There is also a desire for therapy which is less costly and complex to implement and also for therapy which more closely emulates natural physiological feedback and response.

SUMMARY

Illustrative embodiments are at least partially based on the idea that a patient's heart rate is naturally adjusted to match the hydrodynamic impedance characteristics of their arterial system, and that their heart rate is naturally maintained at a frequency so as to utilize these characteristics for increased efficiency and reduced energy expenditure. As the hydraulic or hydrodynamic impedance of the arterial system can be subject to both short term and long term variations, such as by change in the cross-sectional area of a vessel, the elasticity of the arterial wall, the thickness thereof, etc., embodiments of the invention employ the approach of simulating a change in the hydrodynamic impedance characteristics of the arterial system so as to provide a stimulation to drive the heart rate in a desired manner.

Further embodiments employ an observed correlation between heart rate (HR) and blood pressure (BP). These embodiments are at least partially based on the theory supported by clinical observation that blood vessels may increase their elasticity and decrease their compliance to raise a resonant frequency to adapt to the frequency of incident power. This can be achieved coincident with a rise in BP since the elasticity is an upwardly concave function of transmural pressure. Conversely, the arterial system can decrease elasticity and increase compliance to lower the resonant frequency and this is observed to be coincident with a decrease in BP.

Thus, one embodiment is a portable therapeutic medical device comprising a sensor configured to sense a patient's heart rate, a mechanical stimulator arranged to selectively provide mechanical vibrations to tissue of the patient, and a controller in communication with the mechanical stimulator and the sensor wherein the controller evaluates the patient's heart rate and selectively induces the mechanical stimulator to provide mechanical vibrations so as to adjust the patient's native heart rate.

Another embodiment is an implantable cardiac stimulation device comprising an implantable electrical pulse generator, at least one electrode adapted to be implanted within a patient and connected to the electrical pulse generator so as to provide electrical stimulation to the heart of the patient, at least one sensor that senses a parameter indicative of function of the patient's heart, a stimulation component that provides mechanical stimulation to the patient's body, and a controller that uses signals from the at least one sensor so as to induce the at least one electrode to provide electrical stimulation to the heart of the patient and wherein the controller also uses the signals from the at least one sensor to induce the stimulation component to provide stimulation to the heart corresponding to a change in a hydrodynamic impedance of the patient's arterial system.

DETAILED DESCRIPTION

Reference will now be made to the drawings wherein like numerals refer to like parts throughout. The following description is of the best mode presently contemplated. This description is not to be taken in a limiting sense but is made merely for the purpose of describing the general principles of the illustrative embodiments. The scope of the invention should be ascertained with reference to the issued claims. In the description that follows, like numerals or reference designators will be used to refer to like parts or elements throughout.

The illustrative embodiments are based on theories and clinical observations of a hydrodynamic link between cardiac activity and the characteristics of the arterial system. It has been theorized and clinical observations support the idea that the circulatory system can be at least partially modeled by a pressure source (the heart) and a lumped parameter hydraulic impedance, including the arterial system. Pressure waves emanating from the heart, such as upon the ejection of blood upon a contraction, have a wave velocity that can be considered matched to a certain degree with a natural wave velocity of the arterial system. A resonance condition where the cardiac frequency (heart rate), when substantially matched with the natural frequency of the arterial system, can lead to enhanced efficiency of the circulatory transport system. In this resonance model, it is believed that the cardiac output waves can interact with reflected waves in the arterial system in a constructive interference manner so as to increase coronary perfusion. This can lead to an increase in overall circulatory system efficiency and a corresponding reduction in cardiac output energy and improved blood flow throughout the body at reduced blood pressure.

Figure 1:
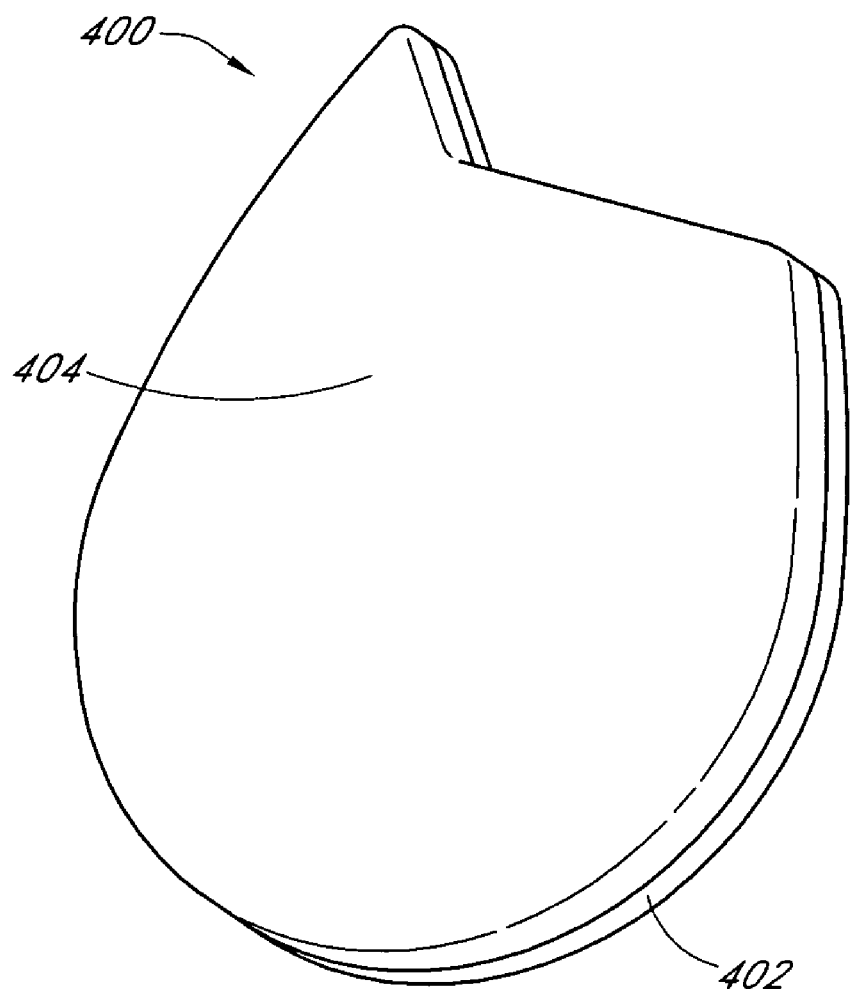
FIG. 1 is a perspective view of one embodiment of a mechanical medical therapy device.

FIG. 1 is a perspective view of an embodiment of a mechanical stimulation device 400 suitable for providing medical therapy. In some embodiments, the mechanical stimulation device 400 is partially or wholly implantable and in other embodiments is configured to be placed and secured in a close proximity to the patient's tissues so as to provide mechanical stimulation thereto.

In one embodiment, the device 400 comprises a substantially rigid housing portion 402 as well as a displaceable housing portion 404. The displaceable housing portion 404 is configured such that the device 400 can automatically spatially displace the displaceable housing portion 404 so as to conduct mechanical vibrations to the patient's tissue. In this embodiment, the displaceable housing portion 404 comprises a region of flexible biocompatible material, however, in other embodiments the displaceable housing portion comprises articulated or jointed portions which can move with respect to the rigid housing portion 402.

Figure 2:
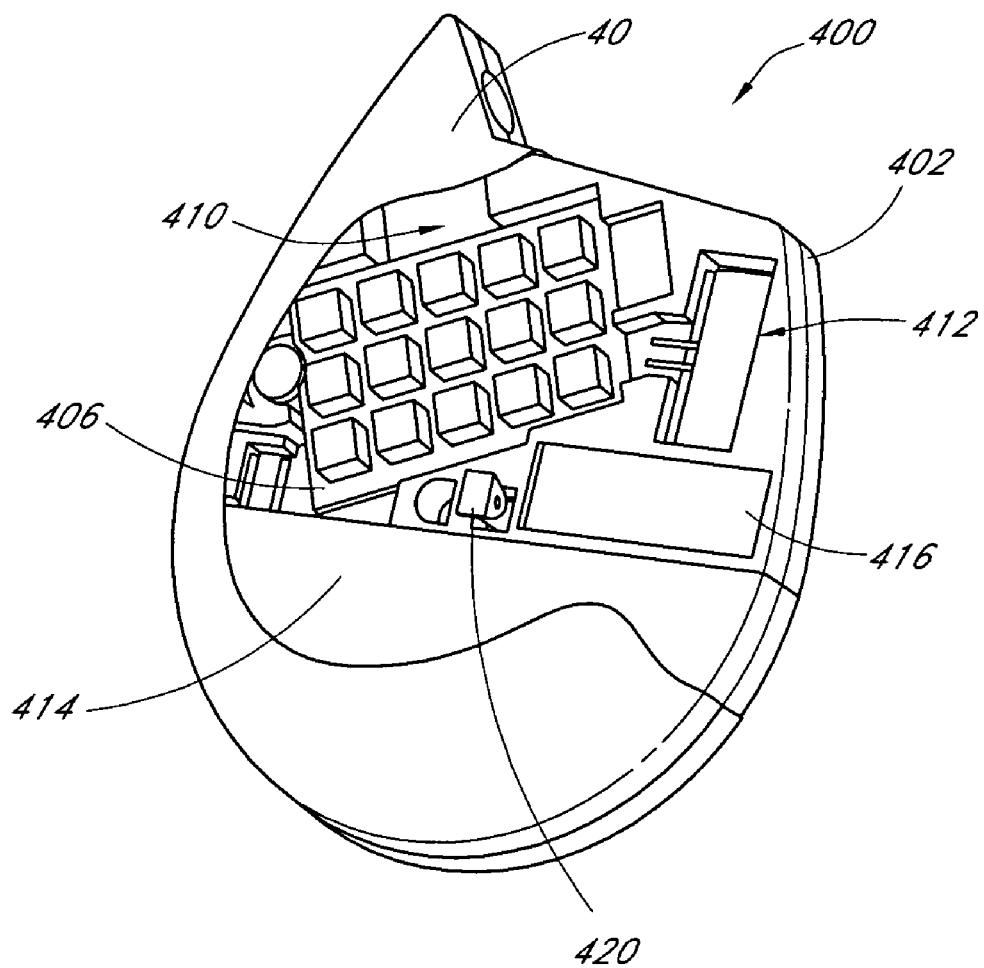
FIG. 2 is a partial cut-away perspective view of an embodiment of a mechanical medical therapy device.

FIG. 2 illustrates in greater detail in a partial cut away perspective view one embodiment of internal components of the mechanical stimulation device 400 configured to selectively provide mechanical therapeutic stimulations. In this embodiment, the device 400 comprises a hybrid electronics assembly 406 which is interconnected to the rigid housing portion 402 via a hybrid support 410. The hybrid electronics assembly 406 determines the timing and control signals for providing mechanical stimulation via the device 400.

The device 400 also comprises a motor 412 which provides rotary motion, preferably in a manner which requires relatively low power consumption as well as in a manner with relatively low levels of electromagnetic interference. A battery 414 is provided which, in this embodiment, provides electrical operating power both to the hybrid electronics assembly 406 as well as to the motor 412.

The rotary output of the motor 412 is conveyed to a displacement mechanism 420, in one embodiment via a gear box or drive mechanism 416. The displacement mechanism 420 is interconnected to the displaceable housing portion 404 such that the displacement mechanism 420 can selectively induce the displaceable housing portion 404 to oscillate or vibrate so as to provide mechanical stimulation to patient tissue via contact with the displaceable housing portion 404. In various embodiments, the displacement mechanism 420 can comprise an eccentric or cam profile, a mechanical linkage arrangement, a hydraulic or pneumatic drive cylinder, and/or a linear actuator, such as an electrical solenoid.

In embodiments including the drive mechanism 416, the drive mechanism 416 can provide gear-up/gear-down functionality so as to provide different rotational velocities between the motor 412 and the displacement mechanism 420. In various embodiments, the drive mechanism 416 can include direct mechanical coupling, such as via bevel, hypoid, worm and/or spur gears/gear trains and in other embodiments the drive mechanism can be an indirect mechanical coupling, such as via pulleys and belt and/or chain and sprockets. In other embodiments, the motor 412 is directly connected to the displacement mechanism 420.

Figure 3:
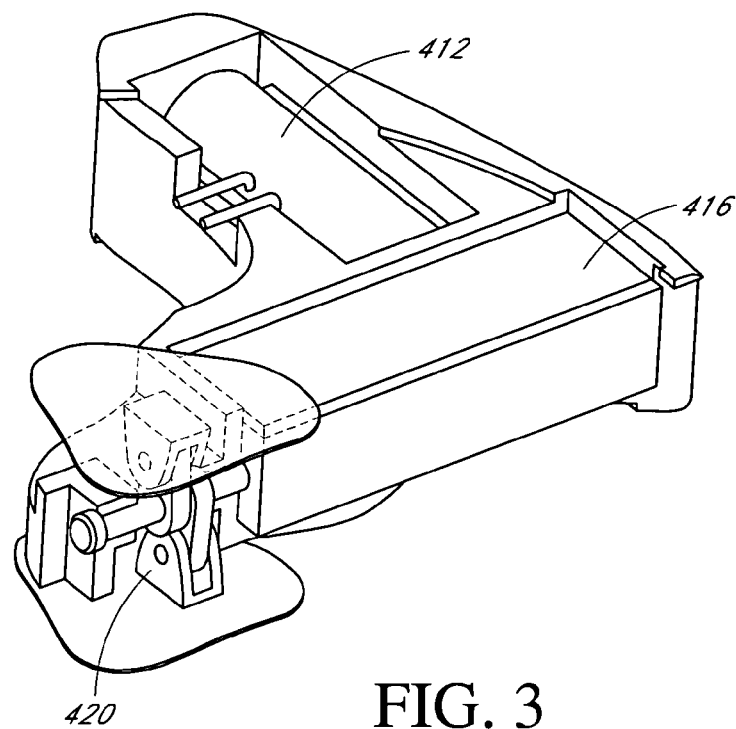
FIG. 3 is a detail of one embodiment of a mechanical displacement system.
Figure 4:
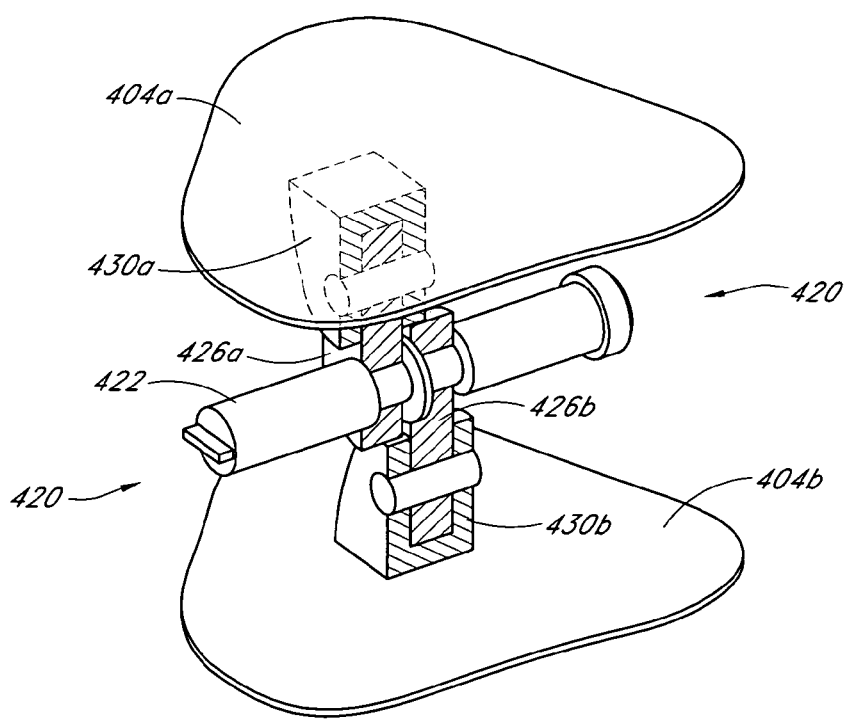
FIG. 4 is a further detail of one embodiment of a displacement mechanism.
Figure 5:
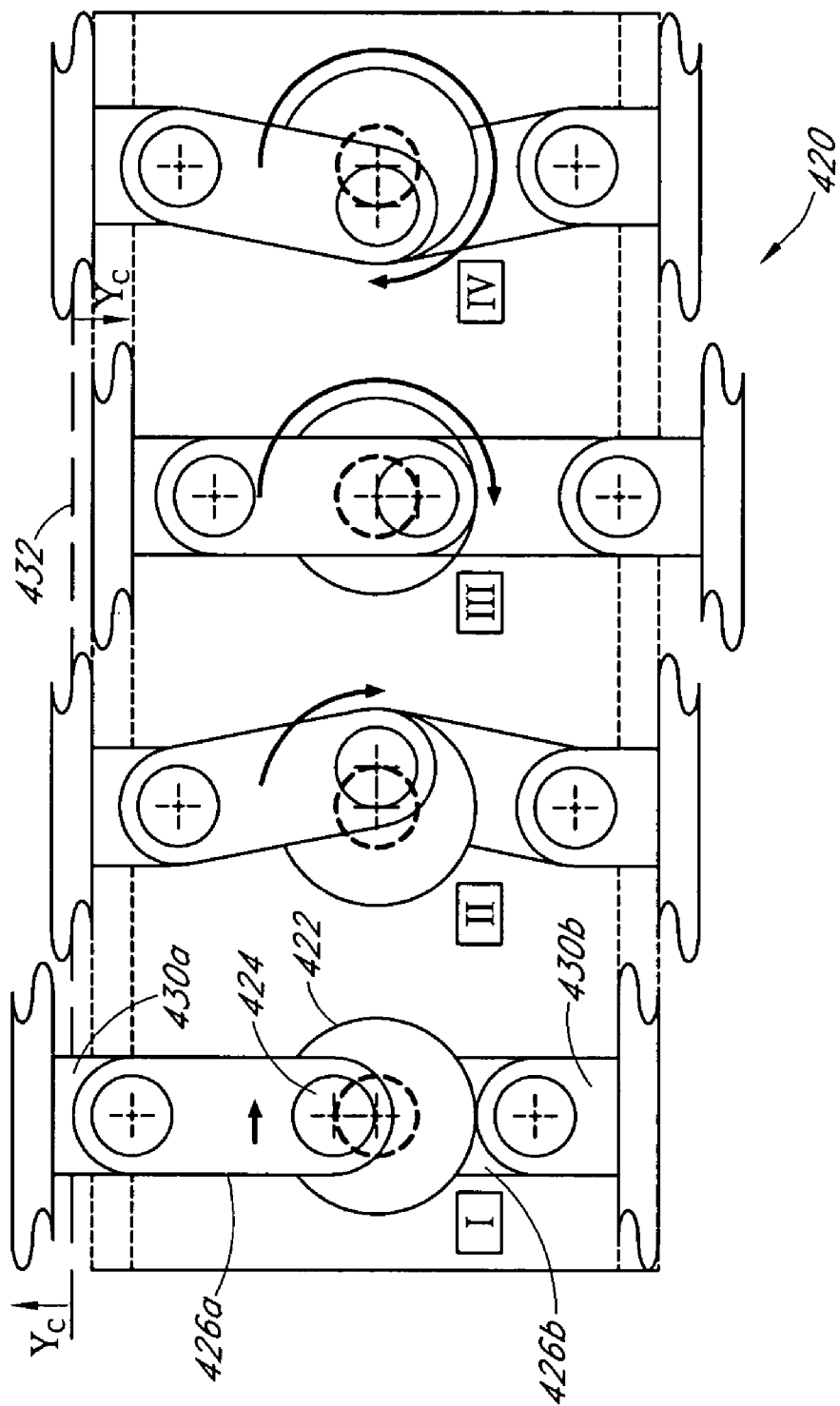
FIG. 5 illustrates an embodiment of operation of the displacement mechanism of FIG. 4.

FIGS. 3, 4, and 5 illustrate in further detail one particular embodiment of a displacement mechanism 420. In this embodiment, the displacement mechanism 420 comprises a drive shaft 422 having one or more, in this embodiment 2, offset crank pin(s) 424. The offset crank pin(s) 424 are arranged with respect to the drive shaft 422 such that rotation of the drive shaft 422 about a major axis thereof will induce the offset crank pin(s) 424 to revolve in a generally circular manner. A first end of corresponding one or more links 426 is connected to the crank pins 424 with an opposite second end of the corresponding links 426 interconnected to a connector 430 which is secured to a portion of the displaceable housing portion 404.

Thus, as can be seen most clearly in FIG. 5, rotation of the drive shaft 422, in this embodiment provided by the rotary motion of the motor 412 as conducted by the drive mechanism 416, induces the crank pin 424 to rotate about a generally circular path and, as the crank pin 424 is interconnected to the link 426 and thus to the connector 430 and displaceable housing portion 404, rotation of the drive shaft 422 induces the corresponding link 426, connector 430 and attached portion of the displaceable housing portion 404 to reciprocate or cyclically oscillate about a neutral position 432.

Thus, the displaceable housing portion 404 is cyclically displaced a distance Yc from this neutral position 432 thereby providing oscillating vibrations or pressure waves to patient tissue in adjacency with the device 400. In this particular embodiment, the device 400 provides these vibrations or spatial displacements on opposed sides via opposing displaceable housing portions 404a and 404b however in other embodiments the mechanical stimulation may be provided at a single side or location of the device 400 without detracting from the scope of the invention.

Figure 6:
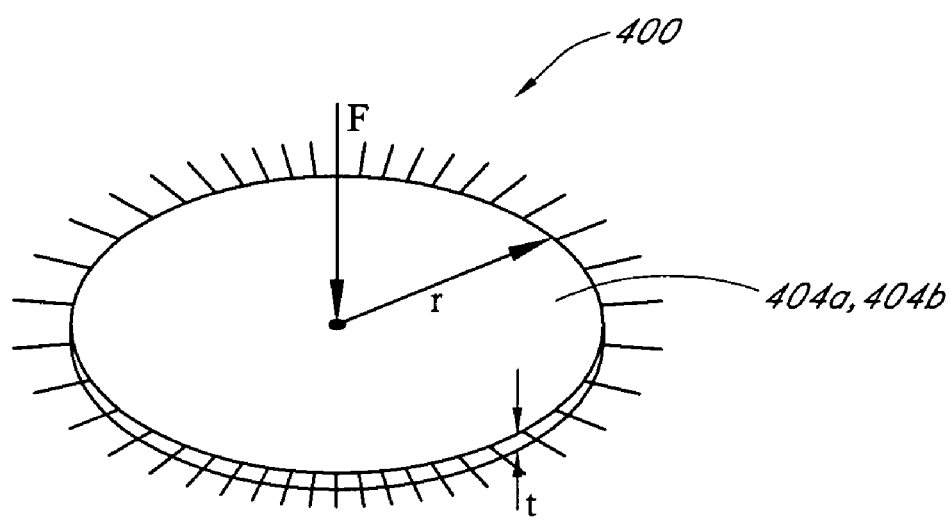
FIG. 6 is a schematic representation of a portion of one embodiment of mechanical stimulation device.

Following is provided a more detailed description with reference to FIG. 6 of one particular embodiment of a mechanical medical stimulation device 400. It will be understood that this is one particular exemplary embodiment and that variations in the dimensions, frequencies, materials, etc. may be appropriate selected for a particular application by one of ordinary skill in the art.

Problem A: It is desired to apply approximately 100 pascals at a frequency of approximately 90 beats or cycles per minute (bpm). The power required is determined as follows:
  Assumptions:
  Device is modeled as a circular plate with fixed edges
  Use maximum elastic modulus for titanium (120 GPa)
  Force is applied at center of plate
  Neglect mass of plate Schematic+Given Data:
(FIG. 6)
r=0.01905 m (0.75 in)
t=0.000254 m (0.010 in)
A=0.00114 m2 (1.767 in2)
$\wp$=4510 kg/m3 (0.163 lb/in3)
E=120 GPa (17.4×106 psi)
V=0.34
Pr=100 Pa (0.0145 psi)
f=1.5 Hz (90 bpm)
ω=2πf=9.42 rad/s

| Terms: | |
|---|---|
| r - radius | D - flexural rigidity |
| t - thickness | f - frequency |
| A - area | ω - angular frequency |
| $\wp$ - density of titanium | $P_O$ - power |
| E - elastic modulus | F - force |
| V - Poisson's ratio | $Y_{center}$ - deflection |
| Pr - pressure | |

Flexural Rigidity Calculation:

$$D = \frac{Et^3}{12(1-V^2)}$$

$$D = \frac{(120 GPa)(.000254m)^3}{12(1-0.34^2)}$$

D=0.185 Nm(1.640 lb$_f$in)
Analysis
Deflection @ center of plate with 100 Pa applied.

$$y_{center} = \frac{Fr^2}{16\pi D} = \frac{PAr^2}{16\pi D}$$

$$y_{center} = \frac{(100Pa)(0.00114m^2)(0.01905m)^2}{16\pi(0.0185Nm)}$$

$y_{center}$=4.450 μn(0.175 mil)
Power $$P_O = F \cdot y_{center} \cdot \omega$$

$P_O$=(0.114N)(4.45μm)(9.42rad/s)

$P_O$ = 4.78μW

Consumption Example 1

Battery, Lithium Iodine, (WGL 9438) 1120052
Capacity: 950 mAh
Output: 2.8 Vdc    Energy Available: 2.600 Wh
Life of Device =

$$\frac{EnergyAvailable}{PowerRequired} = \frac{2.6Wh}{4.78 \times 10^{-6}W} = 5.566 \times 10^5 \ h(63.5 \ years)$$

Design Analysis for Flex Can Drawings

Problem B: The device is to be deflected approximately 0.010" at center at a rate of approximately 90 bpm.

Find: The force and power required are determined as follows.

Assumptions:
same as Problem A
Schematic and Given Data:
same as Problem A
Analysis:
Force @ center of plate with 0.010" of deflection.

$$y_{center} = \frac{Fr2}{16\pi D}$$

$$F = \frac{16\pi D y_{center}}{r^2}$$

$$f = \frac{16\pi(0.185nM)(0.000254m)}{(0.01905m)^2}$$

F=6.5N(1.47 lb$_f$)
Power $$P = f \cdot y_{center} \cdot \omega$$

P=(6.50N)(0.000254 m)(9.42rad/$_s$)

$$\boxed{P = 0.01555W}$$

Consumption Example 2

Lithium Iodine Battery

Energy Available: 2.660 Wh $$\text{Life} = \frac{\text{Energy}}{\text{Power}} = \frac{2.66 \text{ Wh}}{0.015555W} = 171 \text{ h}(7.1 \text{ days})$$

Thus as described above, in one embodiment, the device 400 includes mechanical stimulation components that can provide vibrations of approximately 100 pascals in pressure at approximately 90 bpm corresponding to a net power of approximately 4.8 μW. Assuming 100% energy conversion efficiency, this power could be provided by a standard lithium iodine battery in the device 400 for over 63 years, neglecting other power draws. Thus the device 400 can provide therapy continuously for extended periods of time for treatment of chronic conditions.

In another embodiment, much higher pressure vibrations, such as at approximately 5700 pascals, can be provided for shorter periods, in this embodiment slightly over 7 days, again assuming 100% energy conversion efficiency and neglecting other power draws. The relatively lower pressure vibrations can provide effective therapy for extended periods of time, while significantly higher pressure vibrations can be provided for briefer periods when indicated, for example when it is desired to more rapidly adjust the patient's heart rate/blood pressure.

As previously described, the device 400 can provide therapeutic mechanical vibrations for a variety of patient conditions, including cardiac arrhythmias, however the electrical stimulation capability is not required in all embodiments.

Thus, in various embodiments, the device 400 can be configured solely to provide the mechanical therapy described herein as well as the mechanical therapy in combination with electrical stimulation, such as pacing and/or cardioversion/defibrillation. Depending on the particular application, embodiments can provide a more simplified mechanical therapy device 400 lacking the electrical stimulation capability while providing a simpler, less expensive device 400, for example for treatment of chronic hypertension conditions, as well as other embodiments offering more comprehensive therapy options.

Figure 7:
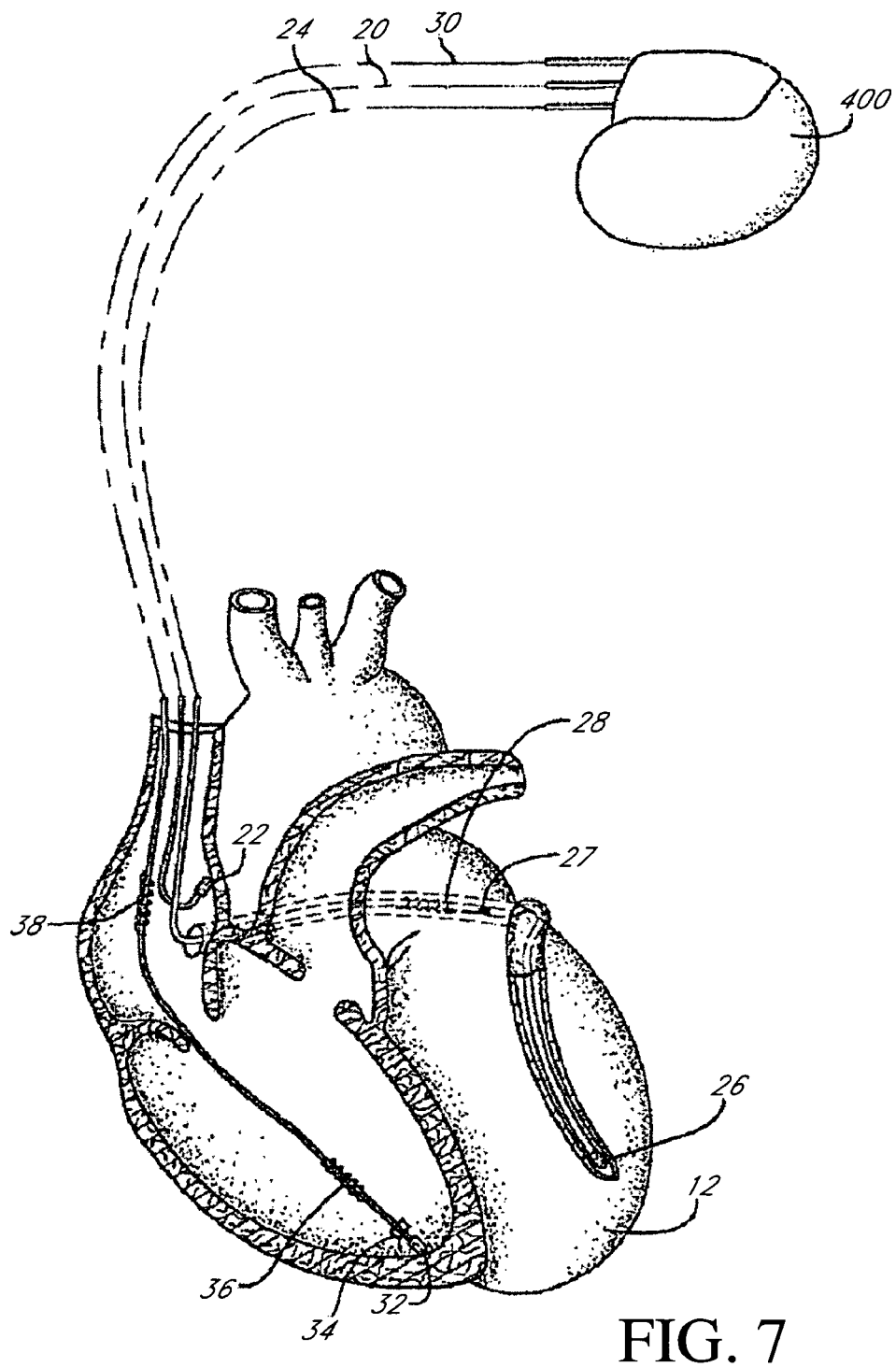
FIG. 7 is a simplified diagram illustrating one embodiment of a mechanical medical therapy device combined with an implantable stimulation device in electrical communication with at least three leads implanted into a patient's heart for delivering multi-chamber stimulation and shock therapy as well as mechanical therapy.

Further description will now be provided of embodiments of a device 400 providing both mechanical stimulation therapy as well as electrical stimulation therapy as indicated. However, it will be understood that one of ordinary skill could readily construct other embodiments of the device 400 having a subset of the components and functionality of this embodiment, such as for a device 400 lacking the electrical stimulation capability. Thus, in one embodiment, as shown in FIG. 7, a medical therapy device 400 comprising an implantable cardiac stimulation device is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the therapy device 400 is coupled to an implantable right atrial lead 20 having at least an atrial tip electrode 22, which typically is implanted in the patient's right atrial appendage.

To sense left atrial and ventricular cardiac signals and to provide left chamber pacing therapy, the therapy device 400 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The therapy device 400 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 8:
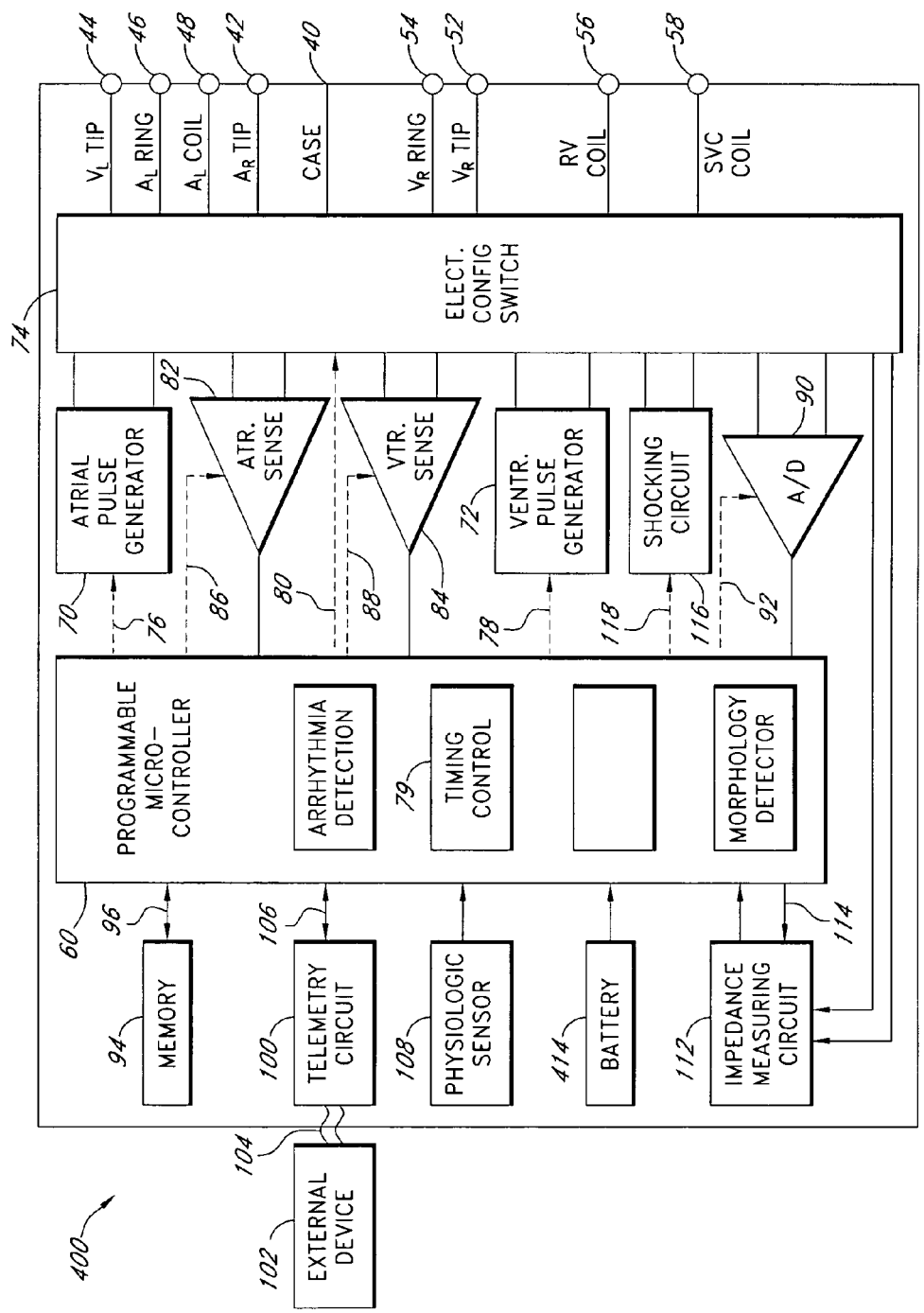
FIG. 8 is a functional block diagram of the multi-chamber implantable stimulation device aspects of the embodiment of FIG. 7 illustrating the basic elements of a stimulation device which can provide cardioversion, defibrillation and pacing stimulation in four chambers of the heart.

As illustrated in FIG. 8, a simplified block diagram is shown of the device 400, which is capable of treating both fast and slow arrhythmias with multi-chamber stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the therapy device 400, shown schematically in FIG. 8, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the therapy device 400 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 8, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 400 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 400 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the therapy device 400 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 400 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 400 (as contained in the microcontroller 60 or memory 94) to be sent to the external device 102 through an established communication link 104.

In the preferred embodiment, the therapy device 400 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. In certain embodiments, the physiologic sensor 108 also comprises a pressure/acoustic sensor such that the physiologic sensor 108 can develop mechanically based determinations of the heart rate and/or blood pressure for determination of delivery of mechanical therapy as well as electrical stimulation.

The therapy device 400 additionally includes a battery 416 which provides operating power to all of the circuits shown in FIG. 8. For the therapy device 400, which employs shocking therapy, the battery 416 must be capable of operating at low current drains for long periods of time and then be capable of providing high-current pulses (for capacitor charging) when the patient requires a shock pulse. The battery 416 must also have a predictable discharge characteristic so that elective replacement time can be detected. Accordingly, the device 400 in preferred embodiments employs lithium/silver vanadium oxide batteries.

As further shown in FIG. 8, the device 400 is shown as having an impedance measuring circuit 112 which is enabled by the microcontroller 60 via a control signal 114.

In the case where the therapy device 400 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Again as previously noted, one of ordinary skill can construct a device 400 employing a subset of the above described features and components, such as a device 400 lacking the electrical stimulation capability and wherein the hybrid electronics 406 comprises a subset of the components and functionality to support the mechanical therapy delivery described above without the electrical stimulation therapy.

Figure 9:
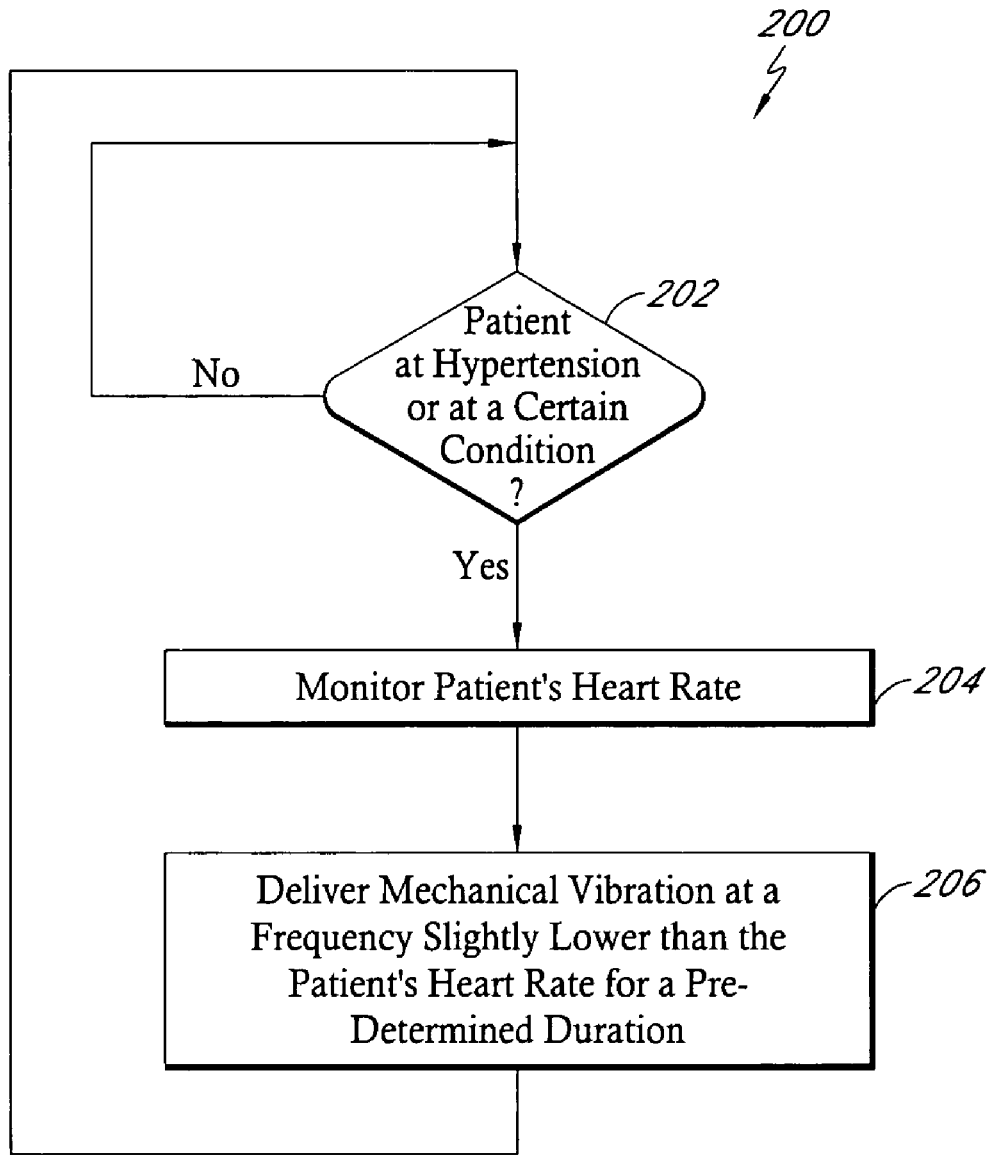
FIG. 9 is a flow chart of one embodiment of determining and delivering therapy directed generally to hypertension.

FIG. 9 is a flow chart illustrating one embodiment of a method of providing medical therapy 200. In certain embodiments, the method 200 would be performed on a long term, ongoing, or chronic basis, and in other embodiments is employed on a short term or acute basis as indicated. The method 200 begins with a decision state 202 wherein an evaluation is made as to whether the patient is experiencing a condition indicating medical therapy. This embodiment of the method 200 is directed generally towards evaluation and treatment of hypertension conditions, however, in other embodiments, other patient conditions can be effectively treated with the method 200 described. Further explanation of this embodiment will be made with respect to hypertension for brevity and ease of understanding.

If a condition is not observed which would indicate medical therapy, the method 200 continues to make the evaluation of state 202 in case such a condition arises. Upon determination that a condition does exist indicating delivery of medical therapy, the method 200 proceeds to a state 204 wherein the patient's heart rate is monitored. The monitoring of the patient's heart rate of 204 can be performed in a variety of known manners, such as detection of electrical signals arising from the cardiac activity such as an intracardiac electrogram (IEGM) and/or a surface electrocardiogram (ECG). In other embodiments, the monitoring of state 204 can follow from acoustic or direct pressure transducers, such as the physiologic sensor 108, which can be either affixed to the patient's body and/or implanted therein.

Following the monitoring of the patient's heart rate of state 204 follows a therapy delivery state 206 wherein mechanical vibrations are generated and delivered to tissue of the patient at a frequency slightly lower than the observed heart rate from state 204 for a determined duration. The mechanical vibration provides spatial perturbations or displacements which are generally cyclical in nature. These vibrations are provided to emulate reflected wave energy from the patient's arterial system and are directed to provide a supplemental feedback mechanism to the patient's cardiac system to induce the heart to slightly lower the rate at which it beats. Thus, the therapy delivery of state 206 comprises a mechanical stimulation of the patient's tissue which propagates throughout the body to the heart 12, but which is indirect in nature, e.g., is not direct electrical stimulation of tissue, such as the cardiac tissue. The mechanical stimulations act in an indirect manner to steer the patient's heart rate and/or blood pressure towards desired values.

In certain embodiments, the therapy delivery of state 206 is provided in a generally strictly periodic manner at a generally symmetric and consistent period, e.g., in a generally sinusoidal manner. In other embodiments, the mechanical vibration provides spatial perturbations or displacements from a set point which are not strictly periodic and/or symmetric in manner, e.g., excursions in opposing directions can occur at asymmetric intervals. In yet other embodiments, the mechanical vibrations are provided with greater high frequency components, such as substantially in a square-wave or saw-tooth waveform. Thus, in various embodiments, the therapy delivery of state 206 can occur in a manner that more accurately tracks actual physiological processes. Thus, use of the terms "frequency", "cyclical", and "vibration" herein does not require that the stimulation component have strictly periodic characteristics, e.g., sinusoidal in nature, and is intended to encompass a variety of complex wave-form and movement characteristics as well as more simple sinusoidal wave forms and movement characteristics.

The delivery of therapy of state 206 in certain preferred embodiments is at a frequency slightly lower than the observed native heart rate from state 204. The particular rate at which the therapy is delivered in state 206 can be programmed by a clinician in accordance with the particular needs of the individual patient. It has been found that improved efficacy of the method 200 is found when the rate of mechanical stimulation provided in state 206 is within approximately 20% of the patient's native heart rate from state 204. In preferred embodiments, it has also been found that increased efficacy of the method is found when the therapeutic stimulation of state 206 is provided for at least a predetermined duration generally in the range of approximately 10 minutes or more. Of course in certain embodiments the therapeutic stimulation of state 206 can be provided for extended periods of time such as for chronic heart rate and/or hypertension therapy depending on the indications for the particular patient.

Figure 10:
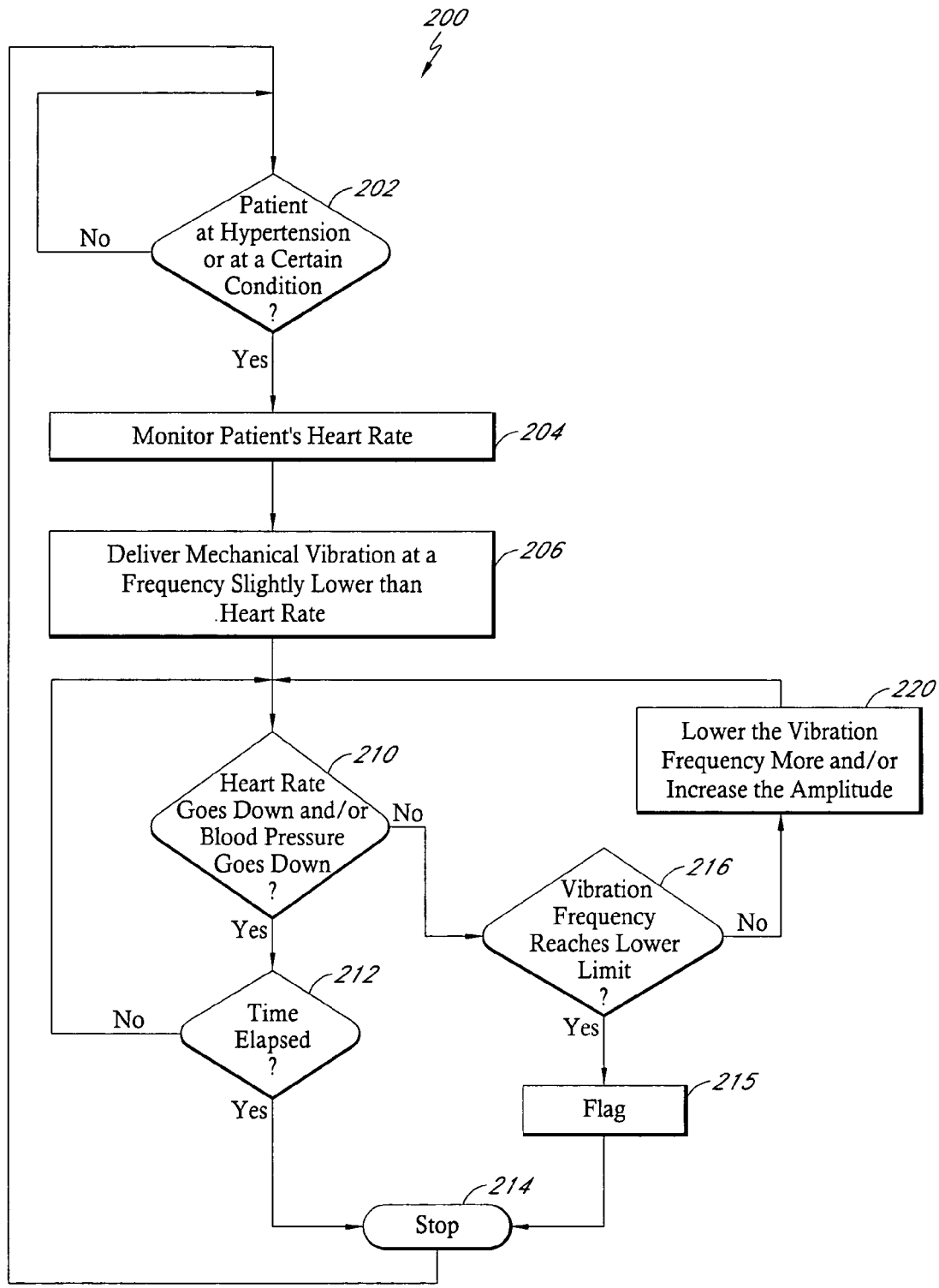
FIG. 10 is a flow chart of a further embodiment of the embodiment illustrated by FIG. 9.

FIG. 10 is a flow chart illustrating further embodiments of a method of determining and delivering medical therapy 200. State 202, 204 and 206 are substantially as previously described and will not be repeated here. Following state 206 is a further evaluation state 210 wherein a determination is made whether a patient's heart rate has gone down and/or whether the blood pressure has gone down as desired. In various embodiments, the determination of state 210 can comprise a determination as to whether or not the heart rate and/or blood pressure has gone down by a discrete amount, a determined percentage and/or to within a threshold window of a desired value. If the desired heart rate and/or blood pressure as determined by state 210 has been reached, a decision state 212 follows wherein a determination is made as to whether a determined period of time has elapsed. State 212 provides the facility in this embodiment to provide an accommodation period to provide a period for the patient to become accustomed to the new lowered heart rate and/or blood pressure and the delay of state 212 provides a period before a successive state 214 where the mechanical stimulation of state 206 is ceased to inhibit a relapse or return to the previously observed undesired condition of state 202. As previously noted, in certain embodiments the therapy of state 206 can be provided for an extended time and the period of time evaluated for in state 212 can be until the patient's next clinical examination, e.g. a period of months where the clinician can determine the continuation or revision of the patient's therapy.

If the determination of state 210 is that the heart rate and/or blood pressure has not gone down to a desired degree, a state 216 follows wherein a determination is made as to whether the intensity of mechanical vibration has reached a determined lower limit. If the lower limit of state 216 has not been reached, a state 220 follows wherein the frequency or rate of delivery of the mechanical stimulation of state 206 is lowered further to provide a stronger stimulus to lower the heart rate and/or blood pressure. In other embodiments, state 220 comprises an increase in the amplitude/energy delivered in order to provide a stronger stimulus. The stronger stimulus in this embodiment can be at the same or also at a lower frequency. If in state 216 the lower limit has been reached, state 214 ceases the therapeutic stimulation and in certain embodiments a flag is set in a state 215 to indicate that the lower limit of intensity of mechanical stimulation of state 206 was reached without a corresponding desired decrease in the heart rate and/or blood pressure. The flag of state 215 can be accessed or automatically provided for further clinical evaluation and/or consideration of alternative therapies, such as via the telemetric link 104.

Figure 11:
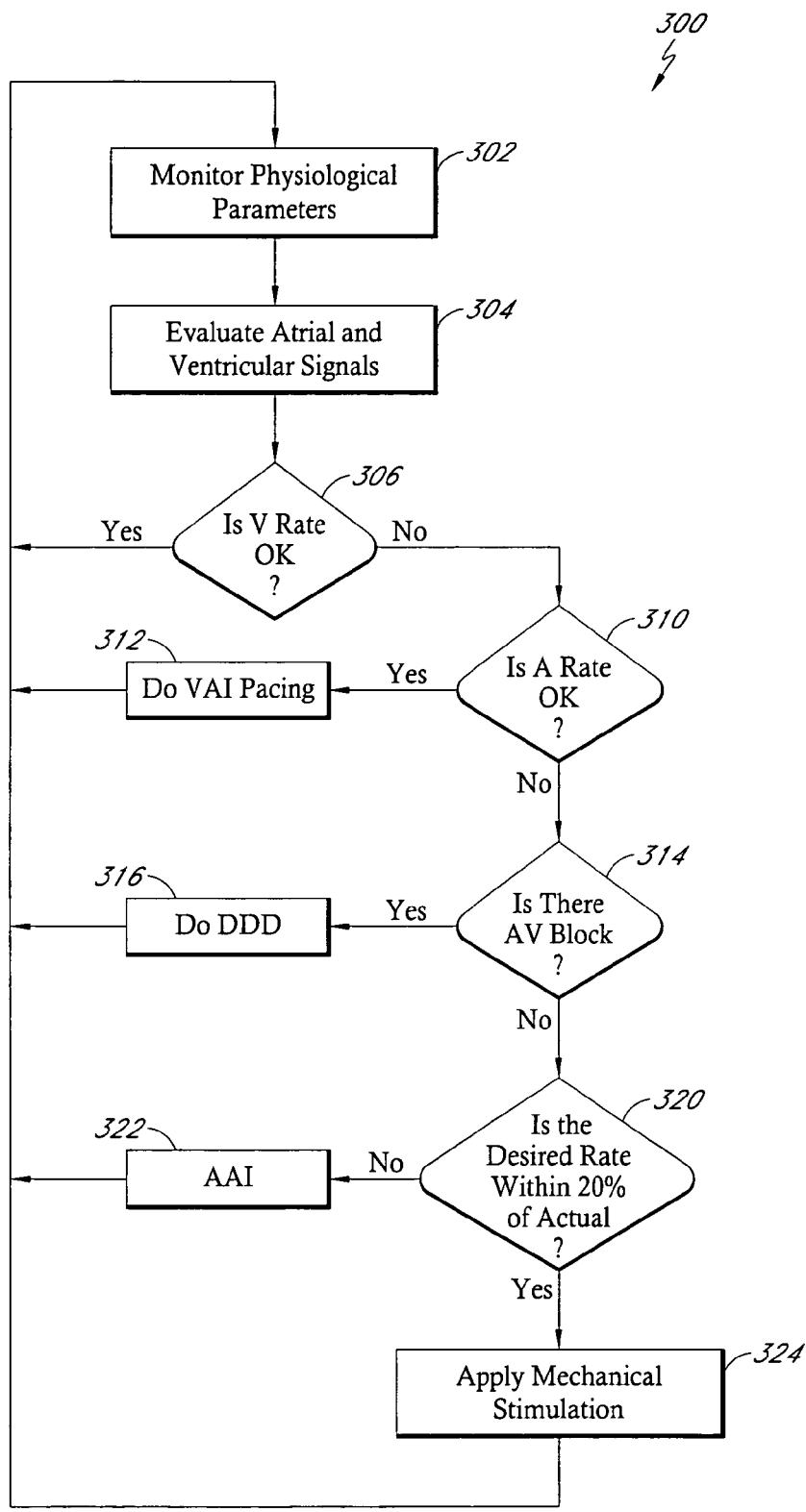
FIG. 11 is a flow chart of one embodiment of determining and delivering therapy directed generally to hypertension as well as cardiac arrhythmia.

FIG. 11 is a flow chart of an alternative embodiment of a method of determining and delivering medical therapy 300. Embodiments of the method 300 are directed generally to determining and providing therapeutic stimulation for observed conditions of cardiac arrhythmia and it will be appreciated that the embodiments of the method 300 can be provided independently as well as in combination with the embodiments of the method 200 as previously described.

Beginning in a state 302, one or more physiological parameters of the patient are monitored, such as via voltage sensors, pH sensors, pressure transducers, temperature sensors, accelerometers, etc. (108 in FIG. 8) which may be implanted or affixed to the patient as appropriate depending upon the particular application. In one particular embodiment, state 302 includes monitoring atrial and ventricular activity. Following in state 304, arterial and ventricular signals are evaluated to determine the activity in at least one each of arterial and ventricular chambers of the heart 12.

In state 306, a determination is made as to whether the observed ventricular rate is within a determined threshold of a desired value. If the ventricular rate is satisfactory, state 306 leads to a repeat of states 302, 304, and 306 for determination of a possible negative result of state 306.

If a negative determination of state 306 is made, e.g., that the ventricular rate is not satisfactory, a determination is made in state 310, whether the arterial rate is within a determined threshold of a desired value. If the determination of state 310 is affirmative, a state 312 follows wherein VAI pacing is provided to attempt to restore satisfactory ventricular rate. If the determination of state 310 is negative, a decision state 314 follows wherein a determination is made as to whether an AV block exists. If the determination of state 314 is that an AV block is present, a state 316 follows wherein DDD pacing is provided. If the determination of state 314 is negative, a decision state 320 follows wherein a determination is made as to whether the desired ventricular rate is within a threshold, in one particular embodiment 20%, of the observed ventricular rate from state 304. If the determination of state 320 is that the desired ventricular rate varies more than the threshold from the actual ventricular rate, a state 322 follows wherein AAA pacing is provided. If the determination of state 320 is that the desired ventricular rate varies by no more than the threshold from the observed ventricular rate, a state 324 follows wherein therapeutic mechanical stimulation is provided to attempt to restore the ventricular rate to the desired value. It will be appreciated that both the observed rate as well as the desired rate can vary depending on the patient's status, such as activity level and medication dosing, and that in certain embodiments the desired rate and determinations made in the method 300 based on this rate varies in a rate responsive manner.

Figure 12:
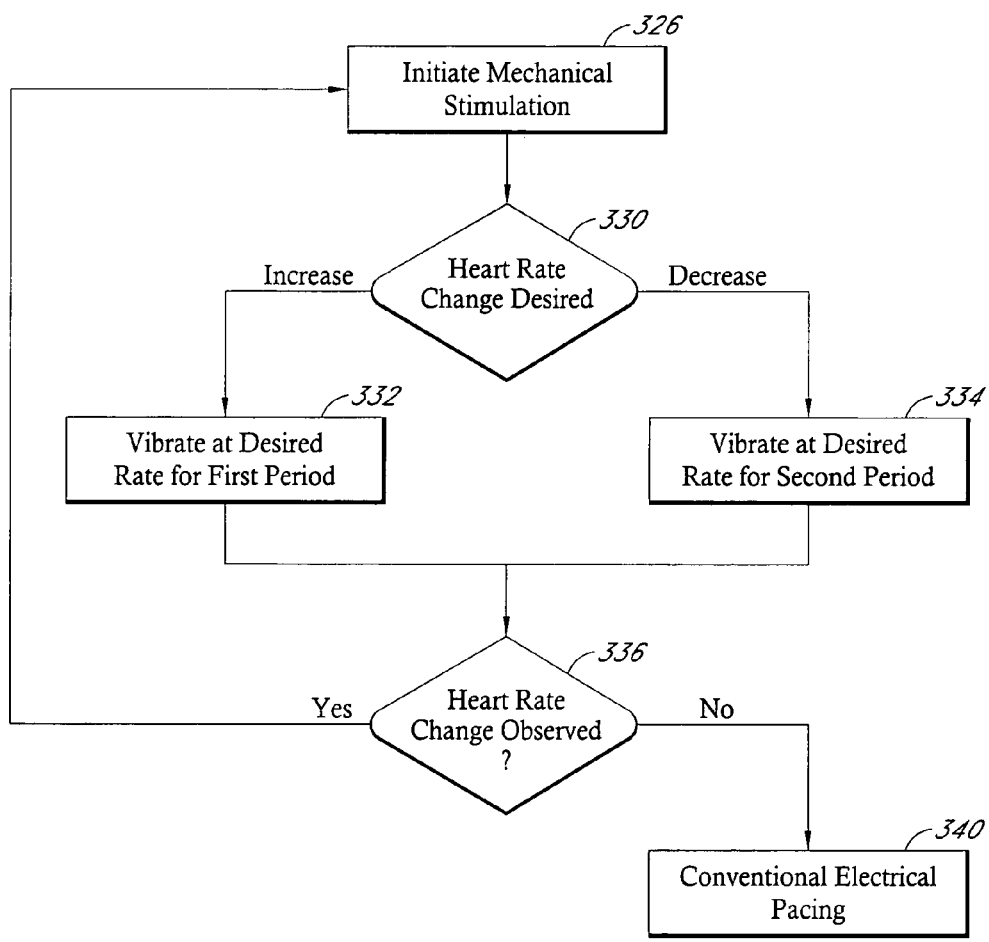
FIG. 12 is a flow chart of a further embodiment of the embodiment illustrated by FIG. 11.

FIG. 12 is a flow chart illustrating in further detail one embodiment of the state 324. The state 324 comprises a therapeutic intervention provided in selected circumstances to provide indirect mechanical stimulation to the patient to attempt to restore desired function while avoiding direct electrical stimulation of the cardiac tissue in the selected circumstances so as to reduce possible negative consequences of the electrical stimulation and to provide a more natural feedback stimulus. Thus, in this embodiment, state 324 begins with the initiation of mechanical stimulation of state 326. The mechanical stimulation of state 326 is substantially similar to that previously described with respect to embodiments of the method 200. Following initiation of the mechanical stimulation in state 326, a decision state 330 follows wherein a determination is made as to whether the change in heart rate desired is an increase or a decrease.

If the change in heart rate desired determined in state 330 is an increase, a state 332 follows wherein the mechanical stimulation or vibration is provided at the desired rate for a first period. If the determination of state 330 is that a decrease is indicated, a state 334 follows wherein the vibration of mechanical stimulation is provided at the desired rate for a second period. As in many applications it has been found that decreasing the heart rate can take a longer period of therapy delivery than to increase the heart rate, in preferred embodiments, the first period is generally shorter than the second period. In one particular embodiment, the first period comprises an interval of approximately two minutes and the second period comprises an interval of approximately ten minutes.

Following either of state 332 or state 334, a decision state 336 follows wherein a determination is made as to whether a change in observed heart rate has been observed. In certain embodiments, the evaluation of state 336 comprises an arbitrary evaluation as to whether the heart rate is within a determined threshold of the desired rate. In other embodiments, the evaluation of state 336 comprises a less stringent evaluation as to whether the observed heart rate has changed in the desired direction and thus the provision of the mechanical stimulation of state 326 at the rate and period of either of state 332 or 334 may be repeated one or more times in an iterative manner of state 324 of the method 300. If the determination of state 336 is negative, e.g., that the heart rate has not reached a desired threshold window after one or more repetitions of the state 324, a state 340 follows wherein conventional electrical pacing is provided. The various indications for delivering electrical pacing are well known in the art and will not be repeated here.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device comprising:
a housing for implant within a patient remote from the patient's heart, wherein a portion of the housing is in contact with tissue remote from the heart and no portion of the housing is in contact with the heart;
an electrical pulse generator within the housing;
a stimulation component within the housing configured to provide mechanical stimulation of the housing which in turn provides mechanical stimulation to the tissue with which the housing is in contact;
at least one electrode adapted to be implanted within a patient and connected to the electrical pulse generator so as to provide electrical stimulation to the heart of the patient;
at least one sensor that senses a parameter indicative of function of the patient's heart;
a controller that uses signals from the at least one sensor so as to induce the at least one electrode to provide electrical stimulation to the heart of the patient and wherein the controller also uses the signals from the at least one sensor to induce the stimulation component to provide mechanical stimulation through the housing and the tissue to the heart corresponding to a change in a hydrodynamic impedance of the patient's arterial system.

2. The device of claim 1, wherein the at least one sensor comprises a pressure sensor arranged to measure the patient's blood pressure.

3. The device of claim 1, wherein the at least one sensor comprises an electrical sensor arranged to measure a heart rate of the patient.

4. The device of claim 1, wherein the controller induces the stimulation component to provide mechanical stimulation through the tissue to the heart so as to adjust the heart rate and blood pressure of the patient towards desired values.

5. The device of claim 1, wherein, when the controller determines that an increase or decrease in the parameter indicative of the function of the patient's heart is indicated, the controller induces the stimulation component to provide mechanical stimulation through the tissue to the heart at a rate greater or less than respectively a native heart rate of the patient to stimulate the increase or decrease in the parameter.

6. The device of claim 1, wherein the stimulation component induces at least a portion of the housing to move so as to provide the mechanical stimulation.

7. The device of claim 1, wherein the stimulation component comprises a displacement mechanism providing mechanical vibrations to the housing.

8. The device of claim 7, wherein the stimulation component comprises a motor generating rotational movement and a crankshaft assembly engaged with the motor such that the rotational movement is converted to reciprocating movement so as to provide the mechanical vibrations.

9. An implantable medical device for delivering therapy to a heart, the device comprising:
- a housing adapted for placement adjacent tissue away from the heart such that no portion of the housing is in contact with the heart;
- a heart-rate sensor;
- a blood-pressure sensor;
- a mechanical stimulator within the housing and operative to induce mechanical vibration of the housing and in turn, mechanical vibration of the tissue away from the heart; and
- a controller within the housing programmed to:
  - determine a heart rate based on signals from the heart-rate sensor;
  - determine blood pressure based on signals from the blood pressure sensor;
  - determine, based on at least one of heart rate and blood pressure, whether therapy is indicated; and
  - upon determination that therapy is indicated, cause the mechanical stimulator to operate such that mechanical vibrations travel from the tissue away from the heart to the heart to change the heart rate.

* * * * *